United States Patent [19]
Reyes et al.

[11] Patent Number: 5,424,959
[45] Date of Patent: Jun. 13, 1995

[54] INTERPRETATION OF FLUORESCENCE FINGERPRINTS OF CRUDE OILS AND OTHER HYDROCARBON MIXTURES USING NEURAL NETWORKS

[75] Inventors: Marilyn V. Reyes; Larry D. Pyeatt, both of Houston, Tex.

[73] Assignee: Texaco Inc., White Plains, N.Y.

[21] Appl. No.: 93,567

[22] Filed: Jul. 19, 1993

[51] Int. Cl.$^6$ ............................................. G01T 1/36
[52] U.S. Cl. ........................................ 364/498; 378/45; 250/372; 395/929
[58] Field of Search ............... 364/497, 498; 399/911, 399/928, 929; 378/53, 45; 250/372

[56] References Cited

U.S. PATENT DOCUMENTS 3,394,139  1/1976  Ohata et al. .................... 250/308
4,877,583  10/1989  Miwa et al. ..................... 422/73

OTHER PUBLICATIONS

Geophysics: the leading edge of exploration, Round Table, "Waveform recognition using neural networks", Palaz et al., Mar. 1990, pp. 28–31.

*Primary Examiner*—Paul M. Dzierzynski
*Assistant Examiner*—David Vernon Bruce
*Attorney, Agent, or Firm*—James L. Bailey; Kenneth R. Priem

[57] ABSTRACT

An artificial intelligence system is used with a conglomeration of fluorescence data to provide a method of improving recognition of an unknown from its spectral pattern. Customized neural network systems allow the ultimate organization and resourceful use of assumption-free variables already existing in a total scanning fluorescence database for a much more comprehensive, discrete and accurate differentiation and matching of spectra than is possible with human memory. The invention provides increased speed of fingerprinting analysis, accuracy and reliability together with a decreased learning curve and heightened objectivity for the analysis.

5 Claims, 8 Drawing Sheets

INTERPRETATION OF FLUORESCENCE FINGERPRINTS OF CRUDE OILS AND OTHER HYDROCARBON MIXTURES USING NEURAL NETWORKS

BACKGROUND OF THE INVENTION

1. Field of the Invention

The present invention pertains to a neural network used for matching fluorescence "fingerprints" of unknown hydrocarbon mixtures with a library of known and previously identified "fingerprints".

2. The Prior Art

A technique for developing a "fingerprint" of an unknown hydrocarbon mixture by fluorescence scanning has become an important and reliable tool for identifying complex mixtures of aromatic hydrocarbons, such as crude oils and refined petroleum products. Such fingerprinting can be an efficient technique for identifying, characterizing and classifying the source of unknown hydrocarbons. The fingerprint is obtained by exciting a sample with varying wavelengths of light in the UV region and measuring the intensity of the resulting fluorescence emissions. A total scan results in a unique three-dimensional fluorescence spectra.

Spectral features of different types of polyaromatic compounds and mixtures have been found to correlate very well with their respective physical and chemical properties. Spectral fingerprints have helped in characterizing unknown fluorescent substances and to differentiate them from crude oils. They have also been used to relate a sample to its source.

As the variety of samples examined has increased, the interpretation of fingerprints has become complicated. Visual comparison of the normal emission scans has been aided by the processes of spectral subtraction and by taking higher order derivatives. However, these processes of differentiation are limited to the small number of known spectra that the human memory can hold. Whereas it is possible to increase the number of correlations, the process becomes tedious and time-consuming. Even then, the accuracy is not all it can be.

Recognition of spectral patterns is more accurately interpreted by manipulation of 3D-data. Several variables have been found to contribute to the accuracy of the spectral interpretation in the course of the development of total scanning fluorescence. What complicates the interpretation of spectra is the discovery of non-linear relations for some variables. Each variable measurement may not be significant by itself, and may contribute differently to the identification or classification of an oil.

There are other data that have been found to increase the accuracy and, at the same time, the ambiguity of predicting properties from spectral fingerprints beyond visual examination of spectra. Calculations of fluorescence yields of the normalized solutions, emission intensity ratios, spectral wavelength ranges, and correlations with other data analyses, such a SARA fractionation and geochemical analyses have contributed significantly to the process of matching fingerprints. SARA stands for Saturates, Aromatics, Resins and Asphaltenes—the four main fractions of classes of compounds that make up the chemical composition of crude oil. SARA Analysis is a chemical process that separates these fractions stepwise by using different organic solvents to isolate each fraction. The analytical technique is called HPLC, which stands for High Pressure Liquid Chromatography.

With the increase in the variables, the growing variety of fluorescent substances to be compared, and the limited capacity of human memory, a method of improving the pattern recognition and interpretation significantly is essential. The application of a neural network system for the existing collection of TSF spectra and information seems to be very promising. The software for the present invention is notable for its resourceful use of assumption-free variables for increased speed of analysis, accuracy and discreteness of data recognition, decreased learning curve, and subjectivity for the analyst.

SUMMARY OF THE INVENTION

The Total Scanning Fluorescence (TSF) technique of the present invention creates "fingerprints" or characterizations of complex hydrocarbon mixtures from three-dimensional fluorescence data. It is an efficient technique for measuring and identifying samples of unknown substances containing any fluorescing hydrocarbon mixture, such as crude oils or refined petroleum products which may be present as contaminants in the environment. Spectral features of different types of polyaromatic compounds and mixtures have been found to correlate very well with their respective physical and chemical properties. Besides typing oils and other aromatic mixtures, the TSF fingerprint has also been used to identify the source rock that generates petroleum.

Manipulations of spectral data have helped define oil characteristics and have increased the accuracy of predicting properties beyond visual examination of the fingerprint. Calculations of fluorescence yields of the normalized solutions, emission intensity ratios, spectral wavelength ranges, and correlations with geochemical analyses (such as SARA fractionation) have contributed significantly to the process of matching fingerprints.

The application of an artificial intelligence system for a conglomeration of fluorescence data provides a method of improving spectral pattern recognition. Customized neural network systems will allow the ultimate organization and resourceful use of assumption-free variables already existing in a TSF database. It will allow a much more comprehensive, discrete and accurate differentiation and matching of spectra than is possible with human memory. The invention provides increased speed of fingerprinting analysis, accuracy and reliability together with a decreased learning curve and heightened objectivity for the analysis.

BRIEF DESCRIPTION OF THE DRAWINGS

The present invention will now be described, by way of example, with reference to the accompanying drawings in which.

DETAILED DESCRIPTION OF THE INVENTION

One of the advantages of the TSF technique over other scanning methods is the increased amount of fluorescence data per sample. The recognition of spectral patterns is more accurately interpreted by the proper selection and manipulation of three-dimensional data. Several variables contribute to the accuracy of the spectral interpretation of TSF. Also, the visual comparisons of the normal emission scans are aided by the processes of spectral subtraction and taking higher order derivatives. However, these processes of differentiation are limited to a small number of known spectra limited by the human memory. Increasing the number of correlations is possible, but the process gets very tedious and time-consuming. Even then, the accuracy is not all it can be.

Figure 1:
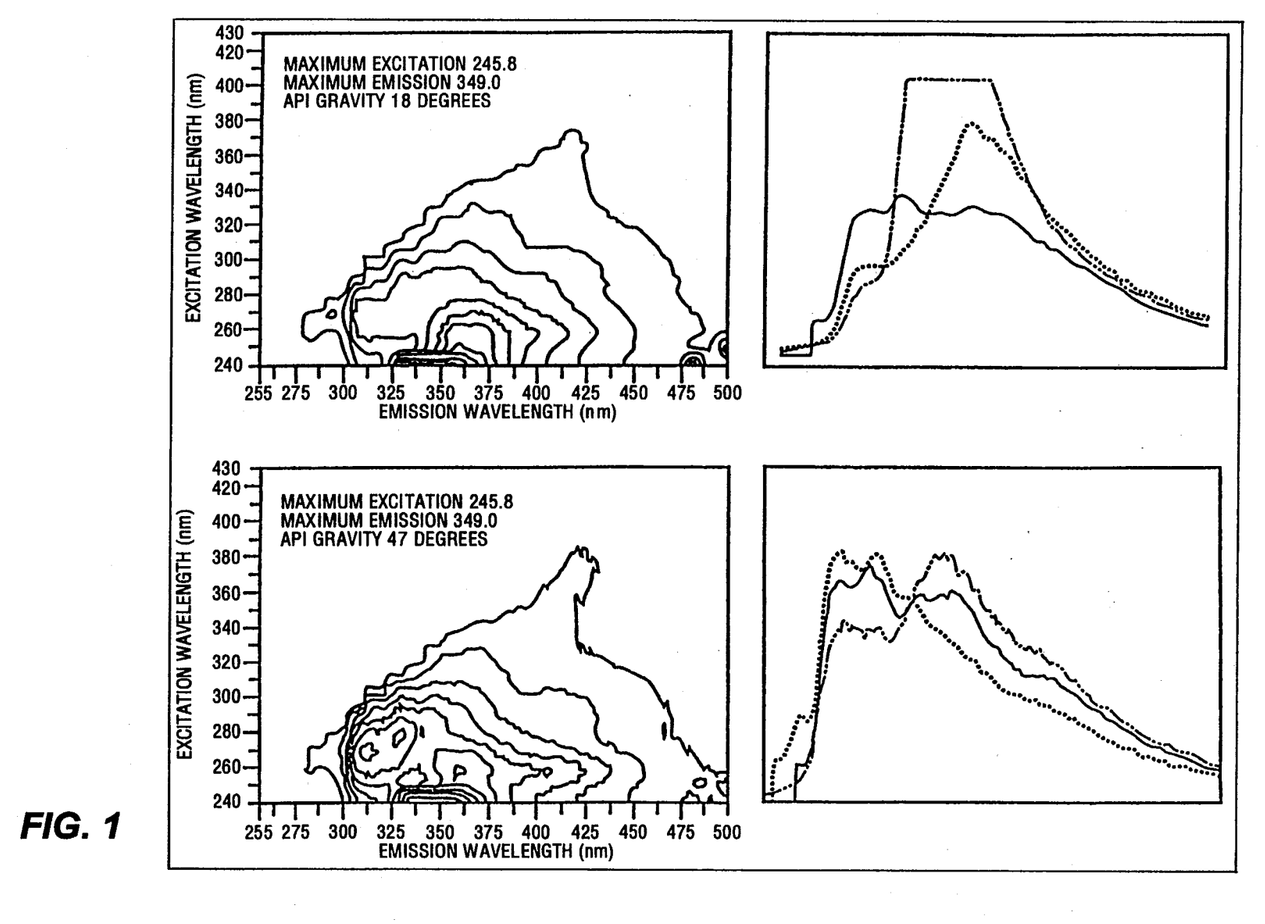
FIG. 1 is a comparison of TSF Spectra of two different crude oils.

With the increase in the number of variables, the growing ambiguities in spectral patterns, and the limited capacity of human memory, a method of significantly improving spectral pattern recognition is essential. For example, in the initial study of ten crude oils of different API gravities, it was found that the region of maximum fluorescence emission can classify the oil type. However, the rule cannot be generalized due to the variability of oil composition creating spectral overlaps among oils. For example, two entirely different oils (shown in FIG. 1), have identical maximum fluorescence peaks but differed significantly in API gravity. One was a heavy oil (18° API), and the other was a light oil, (47° API). Dissecting the spectra of both oils shows the different emission scans. Significant peaks were found present in the lower wavelength region of one of the oils. These are the components which account for one oil being lighter than the other.

Figure 2:
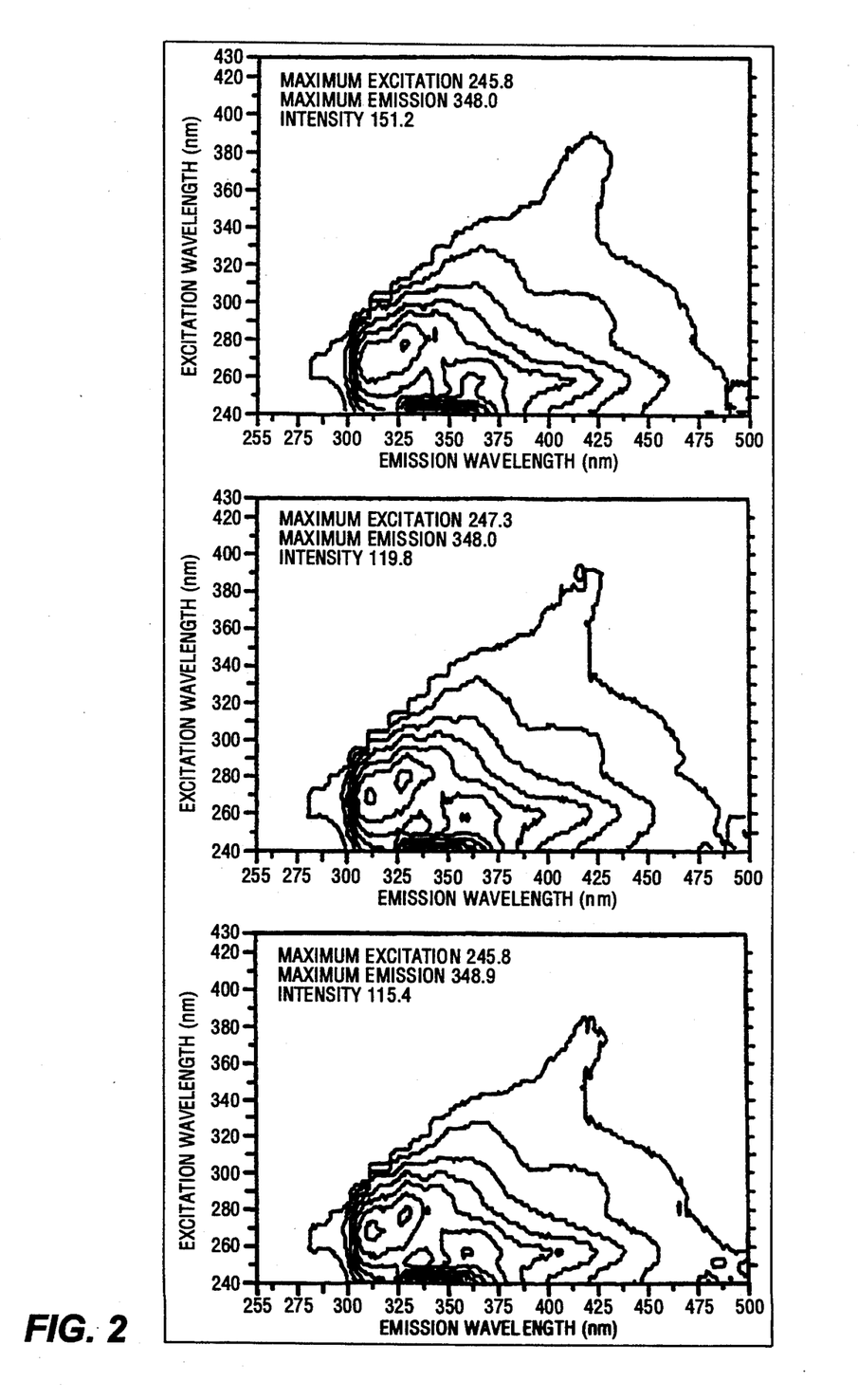
FIG. 2 is a comparison of TSF Spectra of three crude oil samples from different wells in the same field.
Figure 3:
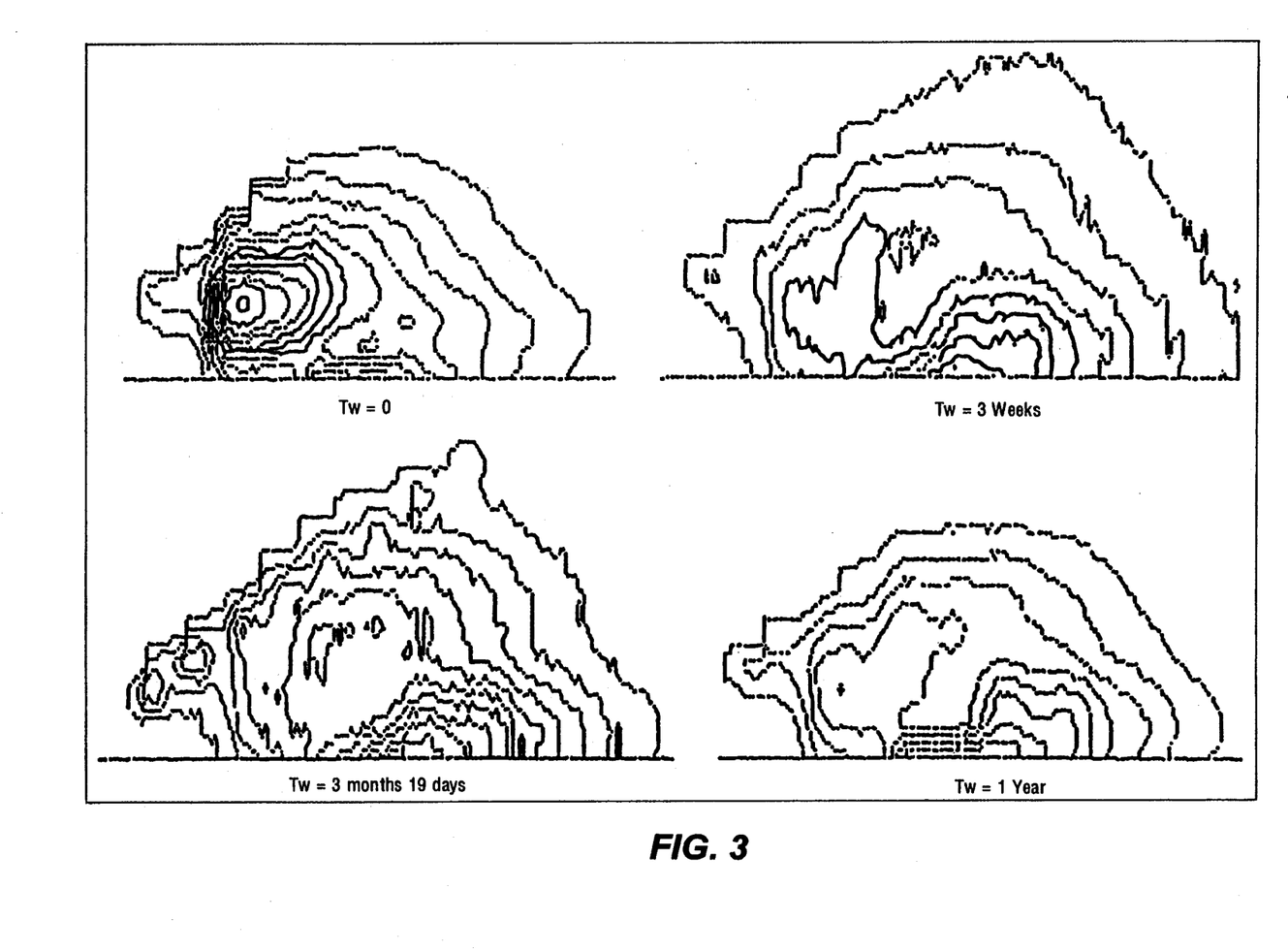
FIG. 3 is an example of the effects of weathering on the spectra of a condensate.
Figure 4:
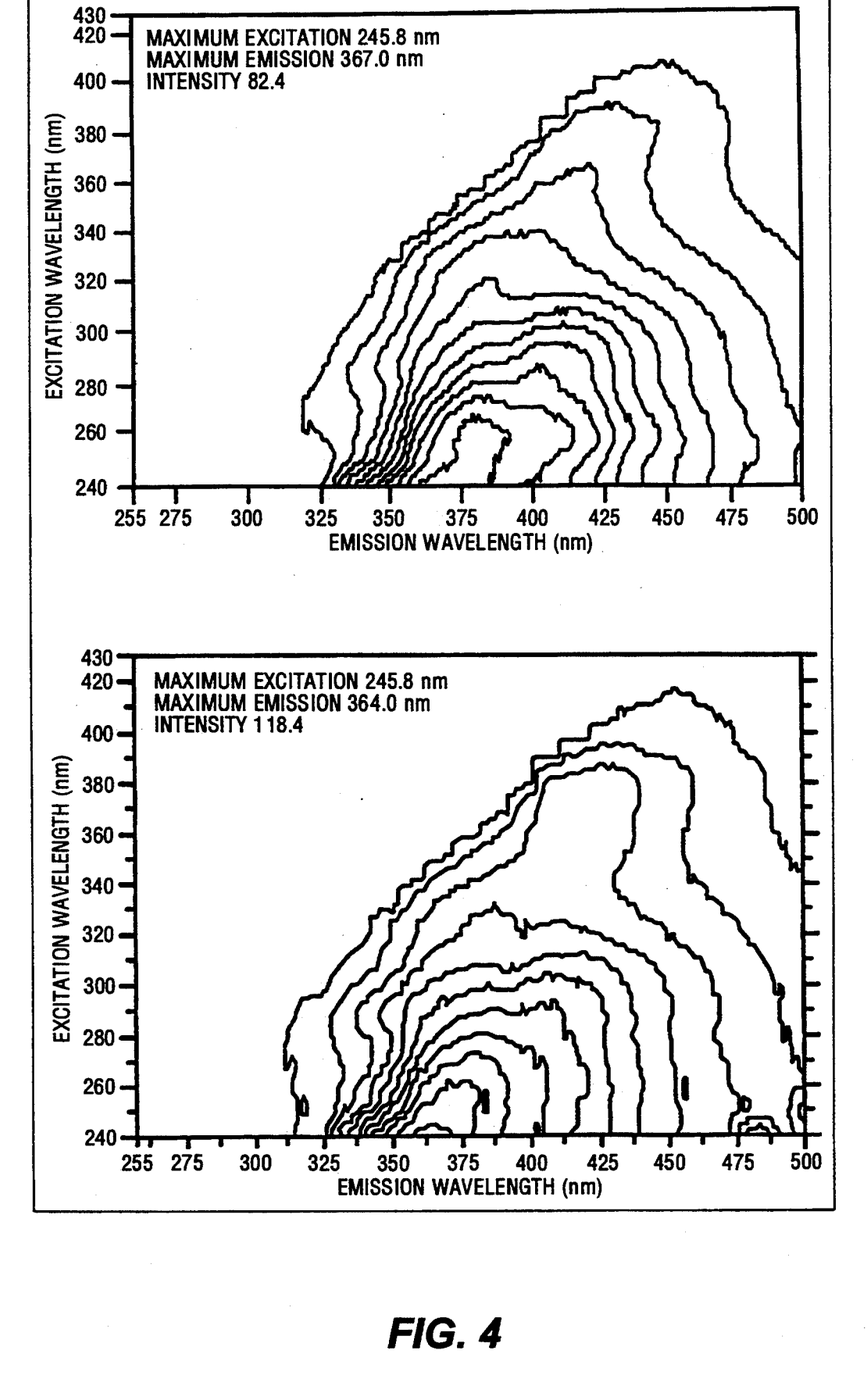
FIG. 4 is a comparison of the TSF Spectra of two different samples.

On the other hand, the same oil can have differences in fingerprints due to a number of reasons, such as the sample matrix, the age of the sample, the manner of sample handling, or the degree of weathering, etc. FIG. 2 shows three spectra with subtle differences. These are oils from different wells in the same field. FIG. 3 shows four different spectra of the same oil weathered under a UV lamp over a period of one year. Also, two entirely different samples can appear to have similar fingerprints, such as the examples of asphalt mud additives and compost material shown in FIG. 4. This spectra is also very close to that of a low API gravity oil. Some of the differences, such as intensity, have not been shown.

Figure 5:
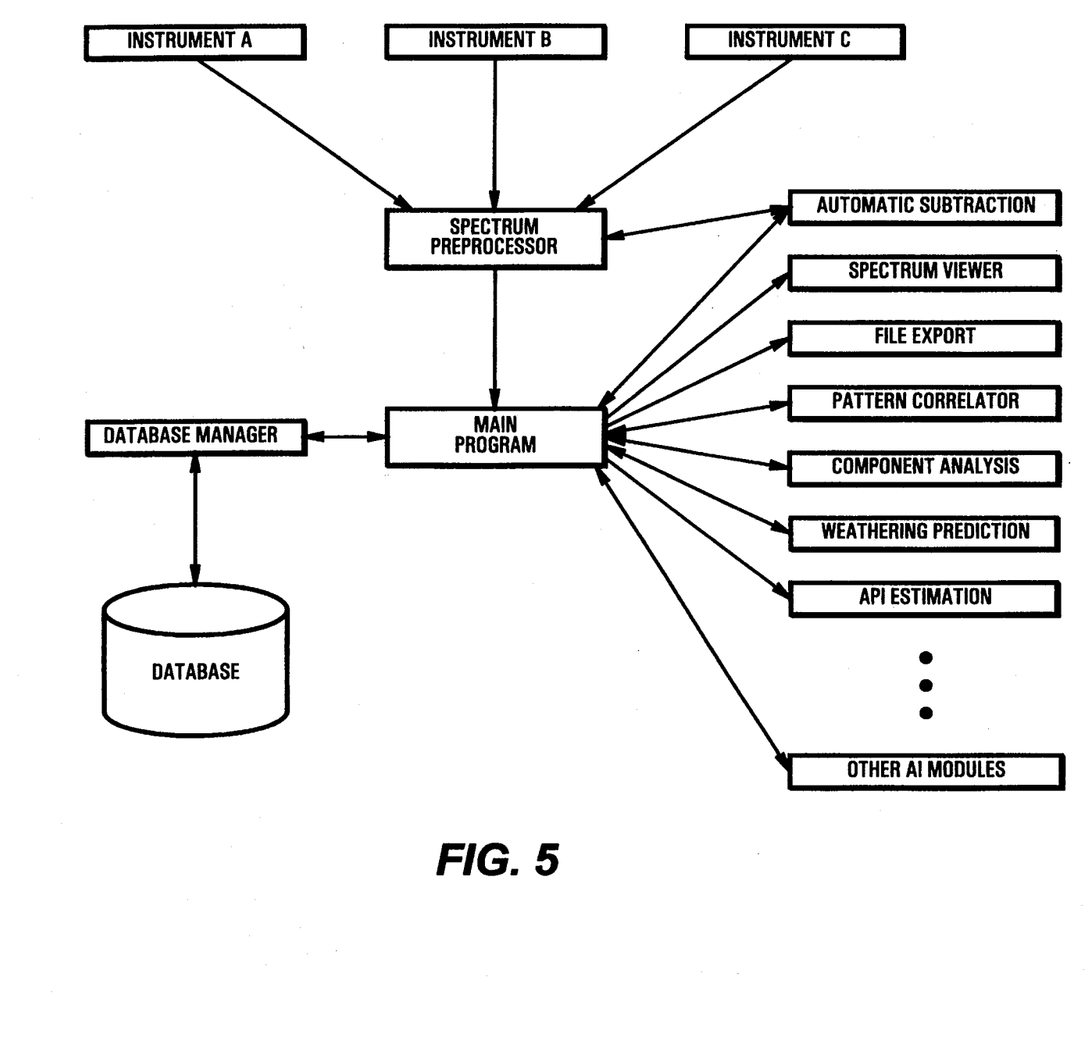
FIG. 5 is an overview of the related software.

The present invention creates an "artificial assistant" for the researcher. The software will do the boring, repetitive tasks which do not require expert judgment, and allow the human expert to concentrate on the important tasks. FIG. 5 shows an overview of the subject software. The new software system can be divided into three major parts, namely a spectrum preprocessor, a database manager, and a set of artificial intelligence subroutines.

Figure 6:
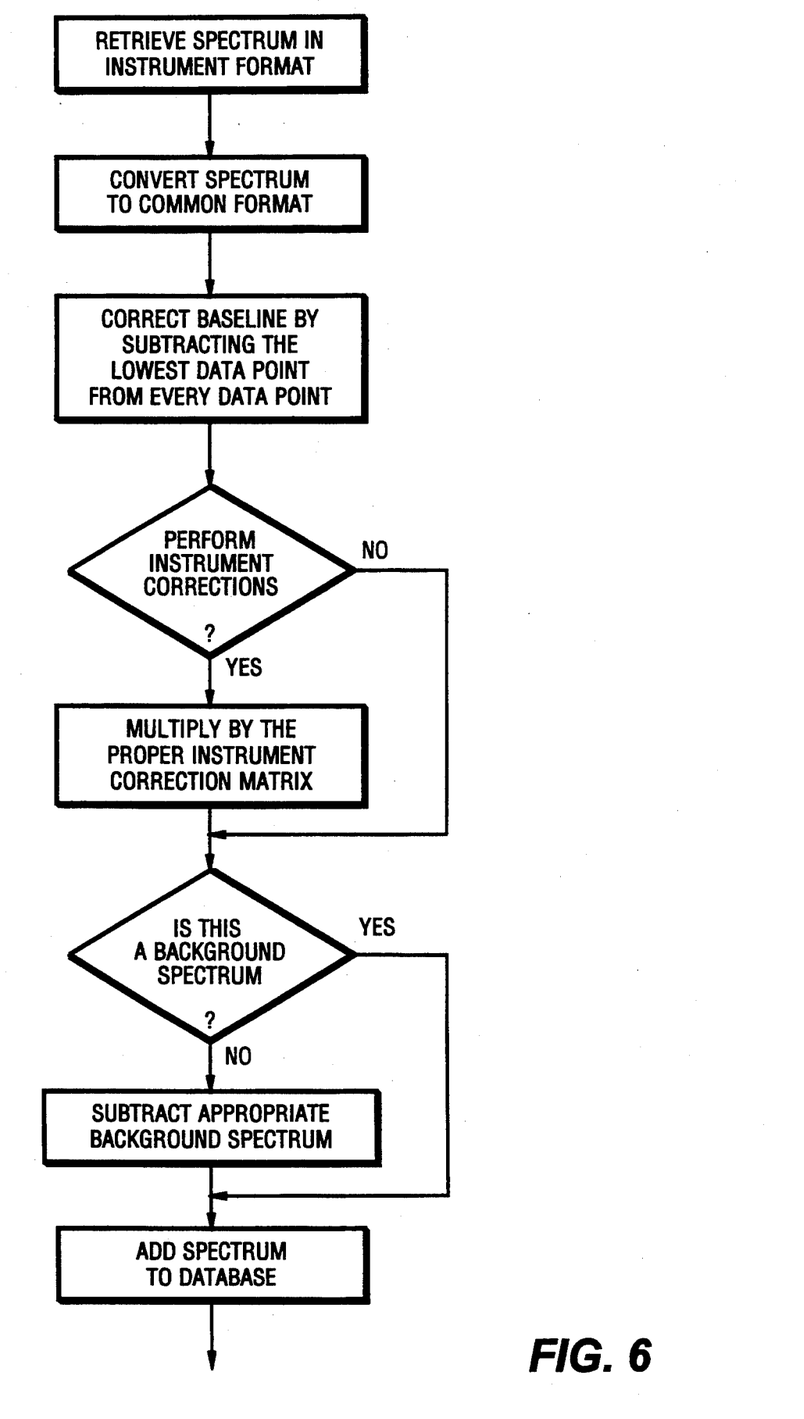
FIG. 6 is a flowchart showing how new spectra are imported into the database.

The spectrum preprocessor receives spectrum data from several different sources, for example the previously mentioned fluorescence detectors. Each data source has its own file format, characteristic background noise, and frequency response characteristics so that one sample passing through each of the different instruments will give different fingerprints. The preprocessor converts each spectrum file to a common format, removes the individual instrument characteristic background noise, corrects for instrument response characteristics, and stores the spectrum in the database. FIG. 6 is a flowchart which describes the spectrum preprocessor.

The database manager portion of the software is used to store, retrieve, view, and print the fluorescence spectra. It may also be used to access additional information which may be stored in external databases. The database manager may provide simultaneous access to the database for several users.

The set of Artificial Intelligence (AI) subroutines is capable of performing a variety of tasks, such as searching to locate similar fluorescence spectras, estimation of API gravity and other geochemical properties from crude oil fluorescence spectra, estimation of the effects of weathering on fluorescence spectra, and automatically determining a subtraction factor for subtraction of one spectrum from another. New AI routines which perform additional tasks may be added at any time. In the preferred embodiment, the AI consists of a minimum set of modules. It is implemented using several standard feedforward and/or recurrent neural networks. The networks are trained with data obtained from the geochemical analysis of known oils. For instance, when training a neural network to estimate API gravity, a set of spectra and their associated API gravities are extracted from the database. Next, a feature vector is derived from each spectrum. The feature vector can be created by a variety of standard techniques, such as subsampling, frequency domain analysis, a Kohonen neural network, or others. Each feature vector and its associated API gravity is then presented to a neural network, which learns the relationship between API gravity and the feature vector. After training, the neural network can estimate the API gravity of any fluorescence spectrum. This technique is not limited to API gravity, but is applicable to other geochemical properties such as lithology, formation age, and others.

The first AI module is used for spectral subtraction. It is sometimes helpful to subtract one spectrum from another. For instance, a sample may contain some crude oil plus a contaminant. It is helpful to remove the part of the spectrum which represents the contaminant, while maintaining the spectral pattern of the crude oil. One of the AI modules is used for automatic subtraction of spectra. If the spectrum of crude oil plus contaminant is represented by A and the spectrum of the contaminant is represented by B, then it is necessary to estimate how much of the fluorescence in A is due to the contaminant. The spectral subtraction $A - xB$, where x represents the relative strength of spectrum B, will result in a new spectrum which represents the crude oil without any contaminant. This spectral subtraction method can be used to remove the background noise from every sample. This procedure is absolutely necessary for the other Artificial Intelligence routines to work well. This subtraction method can also be used to give a human operator a good idea of the relative strength of any spectral component in a sample and to separate low fluorescence values more discretely from background noise. This method is not limited to UV spectra, but can be used for any other signal processing task where there is a predictable background component which must be removed.

A further AI module (the spectral correlation) is used for visual searches of the database. When it is given a spectra A, it searches the database maintained by the database manager module for spectra which look similar to A and indicates, with correlation factors, how close the resulting set of spectra match the original. This allows the human expert to concentrate on only the spectra which are important to solving the current problem, without having to remember hundreds or thousands of spectra and spectral characteristics. This is accomplished using a Grandmother Cell Neural Network, which performs with much the same results as a general pattern matching algorithm. This is accomplished using a Grandmother Cell Neural Network, or any other general pattern matching algorithm such as dot product correlation, Nearest Matched Filter classification, or the Spatiotemporal Pattern Recognizer. This module is also capable of performing its task using higher order derivatives of the original data.

A series of AI modules estimate geochemical properties, such a API gravity, of a sample. This is implemented using several standard feedforward and/or recurrent neural networks. The networks are trained with data obtained from the geochemical analysis of known oils. For instance, when training a neural network to estimate API gravity, a set of spectra and their associated API gravities are extracted from the database. Next, a feature vector is derived from each spectrum. The feature vector can be created by a variety of standard techniques, such as subsampling, frequency domain analysis, a Kohonen neural network, or others. Each feature vector and its associated API gravity is then presented to a neural network, which learns the relationship between API gravity and the feature vector. After training, the neural network can estimate the API gravity of any fluorescence spectrum. This technique is not limited to API gravity, but is applicable to other geochemical properties such as lithology, formation age, and others. This will provide a method for estimating geochemical properties where there is not enough material available for the normal laboratory test. This task is accomplished using standard feedforward neural networks with the back-propagation training algorithm.

Another AI module, used for component analysis, gives the chemical makeup of a polyaromatic mixture by breaking the UV spectra up into its component parts. This AI module may use a modified Hopfield neural network, Simulated Annealing, Genetic Algorithm or some other method for solving systems of simultaneous equations.

Yet another AI module, the weathering predictor, estimates the effects of weathering on a sample from the trend of wavelength coordinate shifts in its fluorescence spectra. This may be accomplished with the use of a feedforward or recurrent neural network with back-propagation training.

Estimation and Subtraction of Background Noise

Turning now to a specific example, Hexane, a solvent which is used to extract and dilute a sample, introduces a characteristic background noise into the data. This noise is very easy to recognize in the spectra and must be minimized if the AI software is to work accurately. Because the instrumentation software adjusts the gain of the fluorescence detectors in the spectrum preprocessor for each sample, the proportion of background noise is not the same for all samples. The instrument software provides a means of subtracting one sample from another, but does not calculate the relative strength of the background component and usually leaves a good deal of noise in the sample. Sometimes, the instrument software actually introduces a negative background component into the data. A method for calculating the background component of a fingerprint has been developed. This method will not only subtract the background accurately, but it can also subtract one fingerprint from another and the method is accurate even if a negative background component is present.

Given a feature vector S which contains some unknown component x of the background feature vector B, we would like to determine x and thereby calculate a new feature vector R such that $$R = S - xB$$

which represents the true fingerprint of the sample. In other words, we want to find out what the fingerprint would look like if we could remove all of compound B from the original sample.

It will be easier to do the math with continuous functions and then convert the results to discrete form for use in digital computation. Let the function $s(t)$ represent the feature vector s, the function $b(t)$ represent the feature vector B, and the function $r(t)$ represent the noiseless feature vector R. The goal then is to find some number x such that $$r(t) = s(t) - xb(t) \tag{2}$$

The problem is that we really don't know what $r(t)$ looks like. However, we can make the assumption the $r(t)$ will be smoothest when x is chosen correctly. The solution, then, is to find a value for x which will make $r(t)$ as smooth as possible. If we let $$f(x) = \int r'^2(t)dt = \int (s^1(t) - xb^1(t))^2 dt \tag{3}$$

then by finding x where $f(x)$ is minimized, we have a very good approximation to the background component. Equation 3 is derived from Regularization Theory. The solution is fairly straightforward.

$$f(x) = \int (s'^2(t) - 2xs^1(t)b^1(t) + x^2 b'^2(t))dt \tag{4}$$

$$f(x) = \int s'^2(t)dt - x \int 2s^1(t)b^1(t)dt + x^2 \int b'^2(t)dt \tag{5}$$

Now, since the integrals are constant with respect to $X_1$ we can replace the integrals and find that $$f(x) = C_1 - xC_2 + x^2 C_3 \tag{6}$$

This equation is perfect for what we want to do. It can be shown that it only has one critical point, which can be proven to be a minimum because $\int b'^2(t)dt$ is always non-negative. The easiest way to find the minimum of $f(x)$, is to find the root of $f'(x)$. $f'(x)$ is a line, and therefore the equation for finding x reduces to $$x = \frac{-C_2}{2C_3}, \tag{7}$$

Substituting the integrals back in, we find that $$x = \frac{-2\int s'(t)b'(t)dt}{2\int b'^2(t)dt} \qquad (8)$$

In order to use this solution on our feature vectors, we must discretize it. The discrete form of equation 8 is $$x \approx \frac{\Sigma S_i B_i - S_i B_{i+1} + S_{i+1} B_{i+1} - S_{i+1} B_i}{\Sigma B_i^2 - 2 B_i B_{i+1} + B_{i+1}^2} \qquad (9)$$

This equation will find the value for x so that all of the background noise can be removed and is general enough so that it can be applied.

It should be noted that Fourier analysis of representative spectral patterns indicates that the algorithm may work better if the derivative of S and the derivative of B are used in the above equation, especially when the zero hertz frequency component of the Fourier transform of the samples is not identical for all of the samples. This situation arises because of variations in the calibration of the instruments which are used to obtain the fluorescence spectra. This is a common problem in signal processing and is often referred to as DC bias. Taking the derivative has the effect of removing the zero frequency (DC bias) component.

Pattern Correlation using the Grandmother Cell Neural Network

Figure 7:
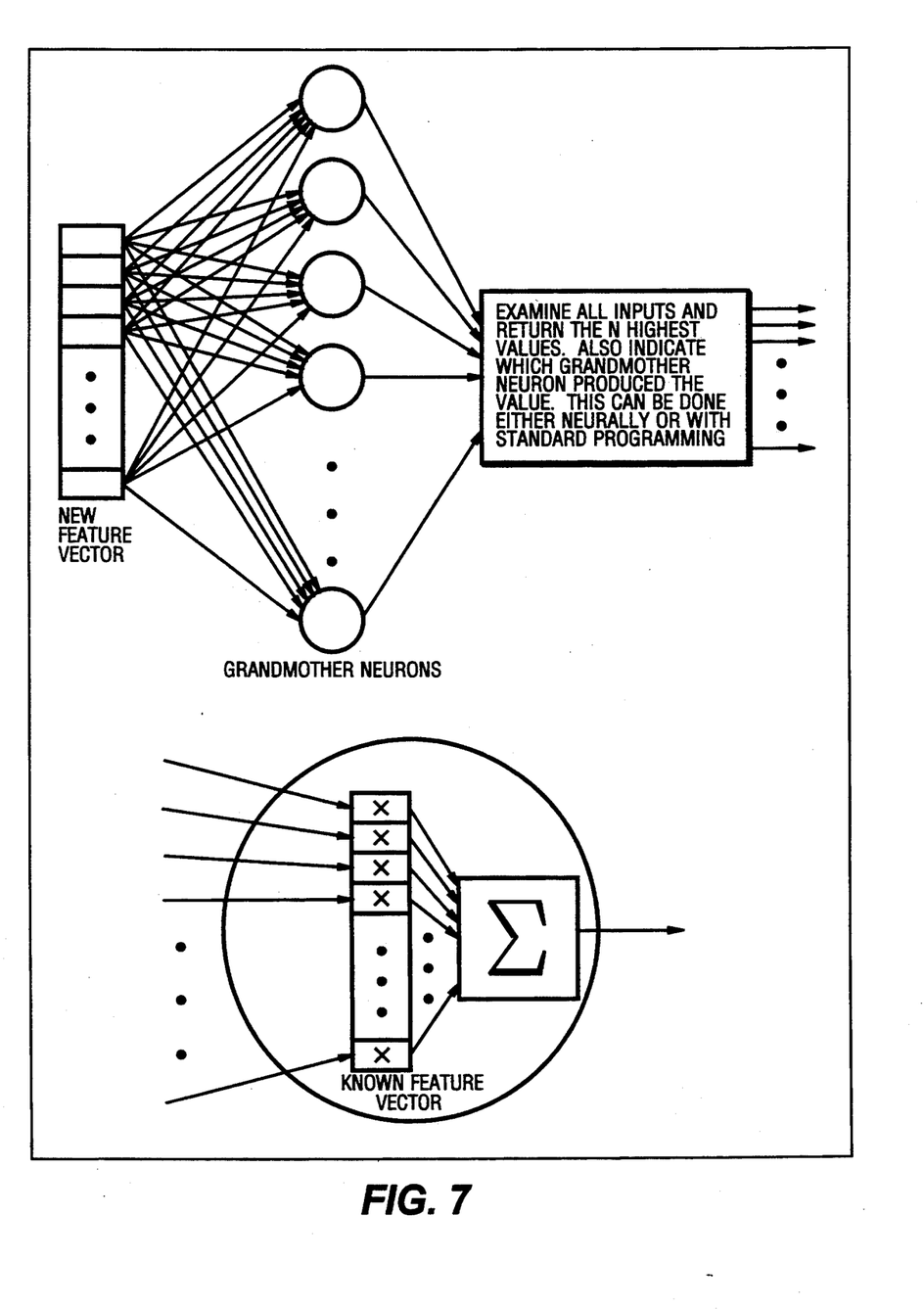
FIG. 7 is a diagram of the Grandmother Cell Neural Network.

FIG. 7 shows a typical grandmother cell neural network. Each grandmother neuron is trained to recognize one specific pattern. When the new feature vector is presented as a target pattern, each grandmother neuron outputs a signal whose strength is proportional to the similarity of the target pattern to the pattern which is has been trained on. Each grandmother neuron is a standard dot product neuron as described by McCulloch and Pitts in "A logical calculus of the ideas immanent in nervous activity". Bulletin of Math. Bio., 5:115–133, 1943, the disclosure of which is incorporated therein by reference and used in many neural network implementations.

The output of a grandmother cell neuron is calculated as a weighted sum of its inputs in the following fashion. For each grandmother cell i in the network, let W be the known feature vector, and let X be the new target feature vector. The output $O_i$ for the cell is calculated as $$O_i = \sum_{j=1}^{M} W_j X_j \qquad (10)$$

where M is the number of dimensions (elements) in the feature vector. Since we are always normalizing the vectors so that $|X|=|W|=1$ we know that $O_i <= 1$ for all i. Thus the output of each neuron i is a number between 0 and 1 which indicates how similar the new pattern is to the pattern which neuron i was trained to recognize.

Figure 8:
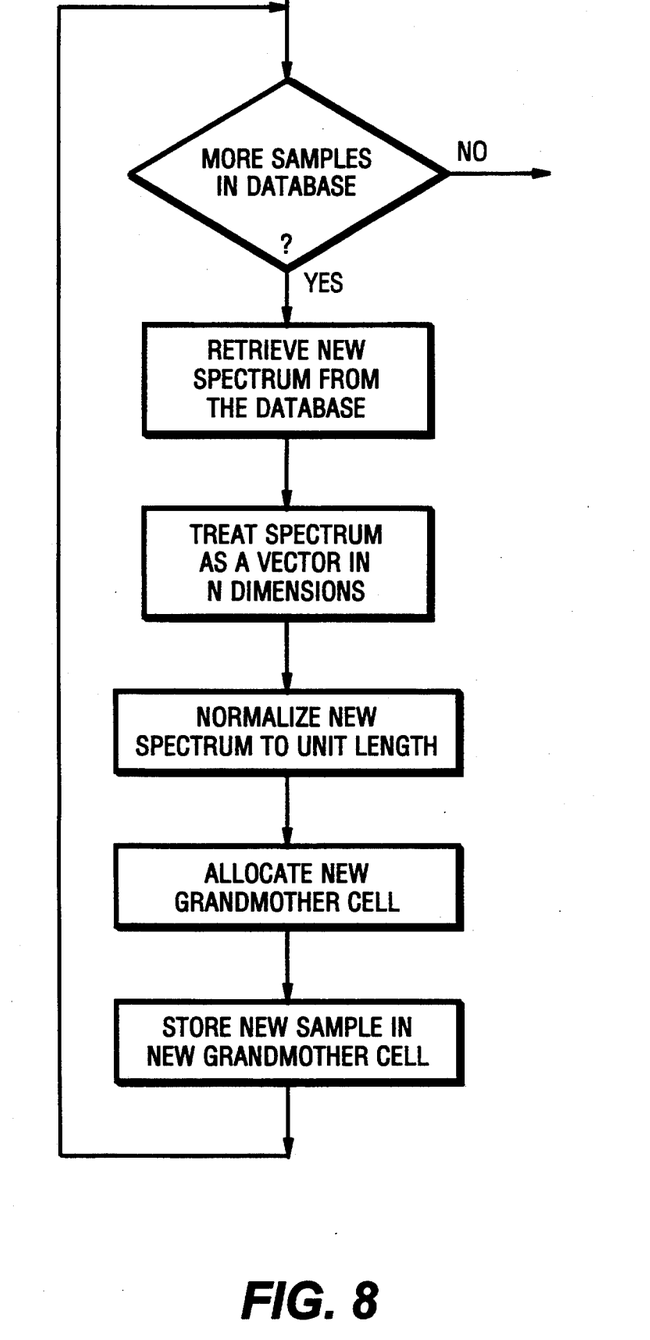
FIG. 8 is a flowchart showing how the Grandmother Cell Neural Network is trained.

FIG. 8 explains how the grandmother cell neural network is trained. Since the computational demands of creating and training a grandmother cell neural network are small, a new network is created and trained each time a correlation is performed.

The present invention may be subject to many modifications and changes without departing from the spirit or essential characteristics thereof. The present embodiment should therefore be considered illustrative and not restrictive of the scope of the invention as defined by the appended claims.

We claim:

1. A system for analyzing and interpreting total scanning fluorescence fingerprints, which are characteristic of complex hydrocarbon fluid mixtures, in order to make a better estimation of composition of the mixture, said system comprising:
   at least one fluorescence detector;
   spectrum preprocessor means connected to receive data from each said at least one fluorescence detector;
   data base manager means connected to said preprocessor means; and
   a plurality of artificial intelligence modules each capable of performing a specific task, all of said modules being interconnected with said data base manager whereby pattern recognition ability of said artificial intelligence modules is utilized by training to identify relationships between fluorescence fingerprints of an unknown fluid sample and known fluorescence fingerprints to estimate the content of fluid being monitored.

2. A system according to claim 1 wherein one of said plurality of artificial intelligence modules subtracts fluorescence data of one sample from the fluorescence data of another sample to eliminate background noise and create a sample data file.

3. A system according to claim 1 wherein one of said plurality of artificial intelligence modules compares the fluorescence fingerprint of the unknown fluid mixture with the fingerprint of known fluid mixtures to predict the content of the unknown mixture.

4. A system according to claim 3 wherein one of said plurality of artificial intelligence modules factors in possible weathering of said unknown mixture.

5. A method using neural networks in analyzing and interpreting fluorescence fingerprints characterizing complex hydrocarbon fluid mixtures comprising the steps of:
   providing at least one fluorescence detector;
   providing a neural network connected to each said at least one fluorescence detector, said neural network having at least spectrum preprocessor means, data base manager means connected to said preprocessor means, and a plurality of artificial intelligence modules connected to said data base manager, each said module being capable of performing a specific task;
   collecting fluorescence data from a fluid sample by said at least one fluorescence detector and feeding said sample data to said neural network;
   comparing said fluorescence sample data to corresponding known standard fluorescence data;
   subtracting fluorescence data of one sample from the fluorescence data of another sample to eliminate background noise and create a sample data file;
   standardizing each sample data file to a common format;
   using this standardized data to "train" the neural network to recognize corresponding characterizing fingerprint data which are likely to be encountered in the study area;
   testing the trained network with known fluorescence fingerprint data; and
   applying to the network fluorescence data from unknown fluid mixtures, whereby comparison with known data is used to make an accurate determination of the content of the unknown fluid mixture.

* * * * *